(12) United States Patent
Paterson et al.

(10) Patent No.: US 9,797,909 B2
(45) Date of Patent: *Oct. 24, 2017

(54) SENSOR

(71) Applicant: Lightship Medical Limited, London (GB)

(72) Inventors: William Paterson, Oxforshire (GB); Nick Barwell, Coventry (GB); Bruce Culbert, Bucks (GB); Barry Colin Crane, Oxfordshire (GB)

(73) Assignee: Lightship Medical Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/276,428

(22) Filed: Sep. 26, 2016

(65) Prior Publication Data

US 2017/0010274 A1 Jan. 12, 2017

Related U.S. Application Data

(63) Continuation of application No. 14/605,315, filed on Jan. 26, 2015, now Pat. No. 9,476,886, which is a (Continued)

(51) Int. Cl.
*G01N 33/66* (2006.01)
*G01N 33/542* (2006.01)
(Continued)

(52) U.S. Cl.
CPC ........... *G01N 33/66* (2013.01); *A61B 5/1459* (2013.01); *A61B 5/14532* (2013.01); (Continued)

(58) Field of Classification Search
CPC .............. A61B 5/14532; A61B 5/1459; A61B 5/14735; G01N 21/6428; G01N 21/7703; G01N 33/66; G01N 33/84; Y10T 436/144444; Y10T 436/206664; Y10T 436/255
(Continued)

(56) References Cited

U.S. PATENT DOCUMENTS 6,387,672 B1 5/2002 Arimori et al.
7,851,225 B2 12/2010 Colvin, Jr. et al.
(Continued)

FOREIGN PATENT DOCUMENTS

JP S63 291596 11/1988
WO WO 2004/007756 1/2004
(Continued)

OTHER PUBLICATIONS

U.S. Appl. No. 61/431,756, filed Jan. 11, 2011, Barwell et al.
(Continued)

*Primary Examiner* — Maureen Wallenhorst
(74) *Attorney, Agent, or Firm* — Fish & Richardson P.C.

(57) ABSTRACT

A sensor for detecting and/or quantifying the amount of analyte in a sample, the sensor including:
a sensing region; and
a barrier layer including a reactive oxygen species (ROS)-quenching, analyte-permeable membrane having an ROS-quenching agent adsorbed thereto;
wherein the sensor is adapted so that the sample enters the sensing region of the sensor through the barrier layer.

22 Claims, 8 Drawing Sheets

Related U.S. Application Data continuation of application No. 14/048,364, filed on Oct. 8, 2013, now Pat. No. 8,940,542, which is a continuation of application No. PCT/GB2013/050407, filed on Feb. 20, 2013.

(60) Provisional application No. 61/611,239, filed on Mar. 15, 2012.

(51) Int. Cl.

| | |
|---|---|
| G01N 33/84 | (2006.01) |
| G01N 21/64 | (2006.01) |
| G01N 21/77 | (2006.01) |
| A61B 5/145 | (2006.01) |
| A61B 5/1459 | (2006.01) |
| A61B 5/1473 | (2006.01) |
| G01N 33/543 | (2006.01) |

(52) U.S. Cl.
CPC ..... *A61B 5/14735* (2013.01); *G01N 21/6428* (2013.01); *G01N 21/7703* (2013.01); *G01N 33/542* (2013.01); *G01N 33/54366* (2013.01); *G01N 33/84* (2013.01); *Y10T 436/144444* (2015.01); *Y10T 436/206664* (2015.01); *Y10T 436/255* (2015.01)

(58) Field of Classification Search
USPC ....... 436/63, 95, 127, 135, 73, 84, 164, 165, 436/166, 174, 178; 435/14, 288.7; 422/82.05, 82.07, 82.08, 82.11, 534, 535, 422/69
See application file for complete search history.

(56) References Cited

U.S. PATENT DOCUMENTS

| | | |
|---|---|---|
| 8,940,542 B2 | 1/2015 | Paterson et al. |
| 2004/0063167 A1 | 4/2004 | Kaastrup et al. |
| 2005/0173245 A1 | 8/2005 | Feldman et al. |
| 2005/0215871 A1 | 9/2005 | Feldman et al. |
| 2005/0221277 A1 | 10/2005 | Kawanishi |
| 2006/0251953 A1 | 11/2006 | Li et al. |
| 2007/0014726 A1 | 1/2007 | Merical et al. |
| 2007/0154466 A1 | 7/2007 | Weber et al. |
| 2007/0191701 A1 | 8/2007 | Feldman et al. |
| 2007/0213611 A1 | 9/2007 | Simpson et al. |
| 2008/0050630 A1 | 2/2008 | Bert et al. |
| 2009/0018418 A1 | 1/2009 | Markle et al. |
| 2009/0177143 A1 | 7/2009 | Markle et al. |
| 2011/0236989 A1 | 9/2011 | Suri et al. |
| 2012/0034550 A1 | 2/2012 | Xia et al. |
| 2013/0040404 A1 | 2/2013 | Crane et al. |
| 2014/0349307 A1 | 11/2014 | Crane et al. |
| 2015/0219663 A1 | 8/2015 | Paterson et al. |

FOREIGN PATENT DOCUMENTS

| | | |
|---|---|---|
| WO | WO 2008/098087 | 8/2008 |
| WO | WO 2008/141241 | 11/2008 |
| WO | WO 2009/019470 | 2/2009 |
| WO | WO 2010/116142 | 10/2010 |
| WO | WO 2010/123972 | 10/2010 |
| WO | WO 2010/123974 | 10/2010 |
| WO | WO 2011/097586 | 8/2011 |
| WO | WO 2011/101624 | 8/2011 |
| WO | WO 2011/101626 | 8/2011 |
| WO | WO 2011/113020 | 9/2011 |
| WO | WO 2013/024260 | 2/2013 |

OTHER PUBLICATIONS

International Search Report (Partial) in International Application No. PCT/GB2013/050407, mailed Jul. 11, 2013, 5 pages.
Peng and Yang, "Designer platinum nanoparticles: Control of shape, composition in alloy, nanostructure and electrocatalytic property," Nano Today, 2009, 4(2):143-164.
Kajita et al., "Platinum nanoparticle is a useful scavenger of superoxide anion and hydrogen peroxide," Free Radical Research, 2007, 41(6): 615-626.
Invitation to Pay Additional Fees in International Application No. PCT/GB2013/050407, mailed Jul. 11, 2016, 5 pages.
International Preliminary Report on Patentability in International Application No. PCT/GB2013/050407, dated Sep. 16, 2016, 13 pages.
International Search Report and Written Opinion in International Application No. PCT/GB2013/050407, mailed Nov. 5, 2016, 20 pages.
Jingling Li et al., "Nonenzymatic glucose sensor based on a glassy carbon electrode modified with chains of platinum hollow nanoparticles and porous gold nanoparticles in a chitosan membrane", Microchimica Acta, Oct. 15, 2010 , 172(1-2):163-169.
Sakura T et al., "Preparation of Platinum—PEG derivatives nanocomposites and study of their reactive oxygen species (ROS) quenching property," Polymer Preprints, Jan. 2005, 54(1):2384, Japan 2005 Society of Polymer Science JP.
Dong Mei Zhou et al., "Poly (phenylenediamine) film for the construction of glucose biosensors based on platinized glassy carbon electrode", Journal of Applied Electrochemistry, Jul. 27, 2010, 40(11):1997-2003.
Oishi et al., "pH-responsive PEGylated nanogel containing platinum nanoparticles: Application to on-off regulation of catalytic activity for reactive oxygen species", Reactive & Functional Polymers, Jun. 21, 2007, 67(7):662-668.

SENSOR

CROSS-REFERENCE TO RELATED APPLICATIONS

This application is a continuation of U.S. application Ser. No. 14/605,315, filed Jan. 26, 2015 (now U.S. Pat. No. 9,476,886), which is a continuation of U.S. application Ser. No. 14/048,364, filed Oct. 8, 2013 (now U.S. Pat. No. 8,940,542), which is a continuation of International Application Serial No. PCT/GB2013/050407, having an international filing date of Feb. 20, 2013, which claims the benefit of U.S. Provisional Application Ser. No. 61/611,239, filed Mar. 15, 2012.

FIELD

This disclosure relates to sensors, membranes for use in the sensors, methods for making such sensors and membranes and methods for detecting or determining the quantity of glucose in a sample.

BACKGROUND

Molecular receptors such as boronates can be used in sensors for the detection and/or measurement of analyte in biological fluids. For example, a sensor may comprise a glucose receptor (the boronic acid) and a fluorophore that acts as the transmitter of the signal. These indicator chemistries can readily be immobilised onto an optical fibre of appropriate diameter, which can then be placed into body fluids or tissue to measure analytes such as glucose.

SUMMARY

Under oxidative stress, it has been found that levels of reactive oxygen species (ROS) such as hydrogen peroxide ($H_2O_2$) can rise. Oxidative stress can arise as a result of an ischemic event or sepsis (e.g. as a result of multi-organ failure) and is also implicated in many diseases (e.g. atherosclerosis, Parkinson's disease, heart failure, myocardial infarction, Alzheimer's disease, schizophrenia, bipolar disorder, fragile X syndrome and chronic fatigue syndrome), thereby raising levels of ROS in the body fluids or tissue of subjects who may require their glucose levels to be monitored, for example in an intensive care environment. ROS in the blood could therefore interfere with sensor indicating chemistry.

It has been found that including a ROS-quenching agent in the sensor could eliminate or ameliorate the interferent effect on sensor chemistry of ROS in the blood. Accordingly, a sensor for detecting and/or quantifying the amount of analyte in a sample can include:
  a sensing region; and
  a barrier layer including a reactive oxygen species (ROS)-quenching, analyte-permeable membrane having an ROS-quenching agent adsorbed thereto;
wherein the sensor is adapted so that the sample enters the sensing region of the sensor through said barrier layer.

The presence of ROS-quenching agents in sensors can oxidise (or otherwise deplete) analyte, which can adversely affect the sensor operation. For example, glucose may be oxidised to gluconic acid. The sensor can thus include a means to address the problem of analyte oxidation in sensors including a ROS-quenching agent. In some embodiments, therefore, the membrane of the sensor can selectively quench ROS over analyte.

In some embodiments, the sensor includes a reactive oxygen species (ROS)-quenching, analyte-permeable membrane, suitable for use in a sensor for detecting and/or quantifying the amount of analyte in a sample, the membrane having an ROS-quenching activity sufficient to quench a solution of $H_2O_2$ having a concentration of 100 ppm or less.

A process for producing a ROS-quenching analyte-permeable membrane suitable for use in a sensor for detecting and/or quantifying the amount of analyte in a sample is also described. The process includes:
  (iii) contacting a barrier layer with a ROS-quenching precursor and a reducing agent;
  (iv) reducing the ROS-quenching precursor to form a ROS-quenching agent on or in the barrier layer; and
  optionally repeating steps (iii) and (iv).

A membrane obtainable or obtained by this process is also described.

In one embodiment the process further comprises, before step (iii):
  (i) contacting a barrier layer with a ROS-quenching precursor and a preliminary reducing agent;
  (ii) partially reducing the ROS-quenching precursor to form a ROS-quenching agent on or in the barrier layer; and optionally repeating steps (i) to (iv). Thus, in this embodiment, the process includes:
  (i) contacting a barrier layer with a ROS-quenching precursor and a first reducing agent;
  (ii) partially reducing the ROS-quenching precursor to form a ROS-quenching agent on or in the barrier layer;
  (iii) contacting the barrier layer with a second reducing agent;
  (iv) fully reducing the remaining ROS-quenching precursor to form a ROS-quenching agent on or in the barrier layer; and optionally repeating steps (i) to (iv). A membrane obtainable or obtained by this process is also described.

The process described herein is particularly beneficial in that it achieves deposition of the ROS-quenching agent within the pores of a membrane, rather than merely on the surface of the membrane. Such deposition within the pores can be achieved even where the membrane has a high aspect ratio, for example an aspect ratio of at least 100, typically at least 150 or 200. Deposition of the ROS-quenching agent within the pores leads to an improved ability of the membrane to quench ROS, since fluid passing through the membrane will be in contact with an ROS-quenching agent throughout the time it is moving through the pores.

A method of detecting and/or quantifying the amount of analyte in a sample is also described. The method can include inserting into the sample a sensor as described herein, providing incident light to the sensing region of the sensor, and detecting the emission pattern of the fluorophore.

Further preferred features and embodiments are described in the accompanying description and the appended claims.

BRIEF DESCRIPTION OF THE FIGURES

FIGS. 9a and 9b depict the results of in vivo testing of a sensor provided herein (FIG. 9b) and a corresponding sensor without a platinised membrane FIG. 9a.

DETAILED DESCRIPTION

Figure 1A:
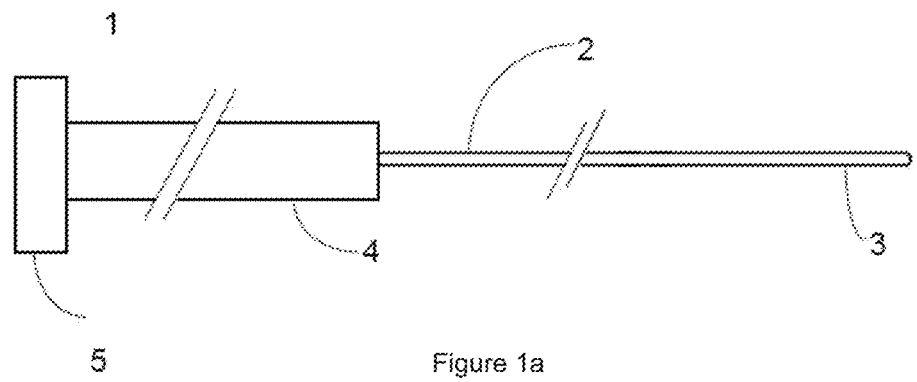
FIGS. 1a and 1b depict a sensor incorporating an optical fibre and a monitor for such a sensor.

As used herein an ROS-quenching, analyte-permeable barrier layer is a material which allows the passage of analyte through the layer but which restricts or preferably prevents ROS from passing through the layer, typically by catalysing its decomposition into chemical species which do not interfere with sensor chemistry (e.g. boronic acid/fluorophore chemistry).

The ROS-quenching, analyte-permeable barrier layer is envisaged for use with any sensor. In some embodiments, the sensor is a glucose sensor, preferably an optical glucose sensor using boronic acid/fluorophore glucose sensing chemistry. The sensor can also be an electrochemical or pH sensor.

The ROS-quenching, analyte-permeable barrier layer may be used with any optical sensor having an optical waveguide for directing incident light onto the sensing region of the sensor. For example, the optical sensor can be a fibre optic sensor. Glucose sensing can be carried out in bodily fluids such as interstitial tissue or blood, although sensing of any aqueous solution may be carried out using the sensors described herein. The particular embodiments described herein are envisaged for use as invasive sensors for insertion into a blood vessel. However, the use of the ROS-quenching, analyte-permeable barrier layer is not limited to such invasive sensors. Non-invasive sensors for in vitro use, implantable sensors, and subcutaneous sensors can also include a ROS-quenching, analyte-permeable barrier layer.

As used herein, the words "include" and "contain", and variations thereof such as "includes", "contains", "including" and "containing", are used in an inclusive sense, i.e. to specify the presence of the stated features but not to preclude the presence or addition of further features.

The Barrier Layer

The barrier layer comprises an ROS-quenching, analyte-permeable membrane having an ROS-quenching agent adsorbed thereto. The ROS-quenching agent may be adsorbed to the surface of the membrane (e.g., the membrane is coated with the ROS-quenching agent), or may be adsorbed to the pores of the membrane (e.g., the membrane may be impregnated with the ROS-quenching agent).

Suitable analyte-permeable membranes which can be coated or impregnated with an ROS-quenching agent and used as the barrier layer in the sensor include semi-permeable membranes such as dialysis membranes and microporous hollow fibre membranes.

In some embodiments, the barrier layer is hydrophilic.

Dialysis membranes are semi-permeable membranes that separate molecules by virtue of their size, shape, hydration and polarity. Dialysis membranes are usually in the form of hollow fibres and are available in materials such as polyarylethersulphone, polyamide, polycarbonate, polyacrylonitrile, polysulphone, polyethersulphone, polyvinylidenefluoride and cellulosic materials or mixtures or modifications thereof.

Microporous hollow fibre membranes are known in the art and include polypropylene hollow fibre membranes. For example, a polypropylene hollow fibre membrane having a pore size of from 0.1 to 0.2 μm, with a porous area of approximately 40% of the surface, a minimum internal diameter of the fibre of 416 μm and a maximum outer diameter of the fibre of 510 μm can be coated or impregnated with an ROS-quenching agent and used as the barrier layer.

In one aspect of this embodiment, a polymer, e.g. a hydrophilic and/or negatively charged polymer, is present within the pores of the membrane. This can be achieved via in situ polymerisation, within the pores of the membrane, of a monomer mixture, for example including one or more hydrophilic monomers and/or one or more negatively charged monomers. Suitable in situ polymerisation techniques are described in international patent application number PCT/GB2011/000209, the content of which is incorporated herein by reference.

In other embodiments, the membrane does not have a hydrophilic polymer present within its pores.

In some embodiments, the membrane used to form the barrier layer in the sensor is a dialysis membrane or a polypropylene hollow fibre membrane.

A semi-permeable membrane used in the barrier layer typically has a pore size of from 1 nm to 1 micron, e.g. from 1 to 20 nm or from 0.1 to 0.5 micron. Typically the hollow fibre polypropylene membrane used to form the barrier layer of the present sensor will have pore dimensions of from 0.1 micron to 0.5 micron, e.g. 0.1 to 0.3 micron such as about 0.2 micron. The dialysis membrane used to form the barrier layer of the present sensor will typically have pore dimensions of 100 nanometers or less. Preferred pore sizes are 1 to 20 nm, preferably 1 to 10 nm, for example about 6 nm.

In some embodiments, the membrane has an aspect ratio of at least 100, preferably at least 150, for example at least 200 or at least 250. As used herein, the aspect ratio is the ratio of the length of each pore (i.e. the thickness of the membrane) divided by the pore diameter. Advantageously, the ROS-quenching agent is distributed along the length of the pore (i.e. not only at the opening of the pore or a part of the pore adjacent the opening of the pore). The techniques for producing the ROS-quenching membrane described are particularly effective at facilitating distribution of the ROS-quenching agent along the length of the pore. The thickness of the membrane is typically at least about 20 micron, for example at least about 30 micron. The thickness may be up to about 50 micron, for example up to about 40 micron. Typically in this embodiment the membrane is a hollow fibre polypropylene membrane.

Semi-permeable membranes are available with different pore sizes relating to the molecular weight cut-off (MWCO) of the membrane. The molecular weight cut-off indicates the maximum molecular weight of molecule which can pass through the pores of the membrane. The semi permeable membrane used in the present sensor has a MWCO such that the analyte can pass through. The semi permeable membrane used in the present sensor is typically a low MWCO material that does not allow materials of molecular weight 6,000 or higher (e.g. to proteins) to pass through, but does allow glucose (MW180) to pass. Preferred membranes have a MWCO of at least 1,000 and preferably no more than 5,000.

For example, the MWCO may be at least 1,500 or at least 2,000, for example no more than 4,000.

The effective pore size and MWCO of the final barrier layer used in the sensor (herein "effective pore size", "effective MWCO") may be lower than those described above as a result of in situ polymerisation, or loading of the ROS quenching agent. The effect of in situ polymerisation on pore size is described in PCT/GB2011/000209 (referenced above), the content of which is incorporated herein by reference. Preferred effective pore sizes for the final membrane are at least 1 nm, e.g. at least 2 nm or at least 4 nm and no more than 20 nm, e.g. no more than 10 nm. Preferred effective MWCO are at least 1,500 or at least 2,000 and no more than 6,000 e.g. no more than 5,000 preferably no more than 4,000.

Measurement of the pore size, or effective pore size, can be carried out by any method known to the skilled person. Typically, the pore size is given as the median pore size for any particular membrane. MWCO can be determined by the diffusion of monodisperse materials of known molecular weights with a fluorescent molecule attached. Materials of gradually increasing molecular weight are passed through the membrane and the diffusion breakthrough can be determined using a fluorimeter as a detector. Examples of suitable monodisperse materials are fluorescein-labelled dextrans available from Sigma-Aldrich in a variety of molecular weights. The effective pore size or effective MWCO may be measured by preparing the final membrane and measuring the pore size or MWCO in the usual way.

In order to provide an acceptable response time (for instance for an intravascular sensor which continuously measures glucose), the barrier layer should preferably be selected so as to provide a 90% response time of a sensor which is no more than three minutes, preferably no more than two-and-a-half minutes.

The 90% response time is determined as the time taken from addition of a known amount of analyte to a sample, to the sensor response reaching 90% of the analyte concentration. This can be measured by contacting the sensor with a zero analyte aqueous solution, adding a known amount of analyte at time to and monitoring the sensor response over time. The sensor response increases over time and the time after $t_0$ at which the sensor reading corresponds to 90% of the added analyte concentration is taken as the 90% response time. In this technique, the analyte is added in such a manner that the change in concentration of the aqueous solution is substantially instantaneous, so there is no time delay due to, for example, dissolution of the analyte. Thus, analyte is typically added in liquid or concentrated solution form, with stirring.

ROS Quenching Agent

The ROS-quenching agent used in the barrier layer can be any substance capable of catalysing the decomposition of reactive oxygen species such as $H_2O_2$.

The decomposition of $H_2O_2$ into chemical species which do not interfere with sensor chemistry (e.g. boronic acid/flurophore chemistry) can occur by disproportionation to water and oxygen gas:

$$2H_2O_2 \rightarrow 2H_2O + O_2$$

Suitable substances capable of catalysing the decomposition of ROS such as $H_2O_2$ include transition metals, transition metal compounds and enzymes.

Typically, the transition metal used as the ROS-quenching agent is a metal of Group 10 or 11 of the Periodic Table, e.g. nickel, palladium, platinum, copper, silver or gold. Preferably, the transition metal used as the ROS-quenching agent is palladium, platinum, gold or silver. More preferably, the transition metal used as the ROS-quenching agent is platinum. An alloy of two or more metals, such as an alloy of a transition metal of Group 10 or 11 with another metal, or an alloy of two or more Group 10 or 11 transition metals, may also be used. Alloys of gold and silver are particularly envisaged.

Typically, the transition metal compound used as the ROS-quenching agent is a compound of a metal of Group 7 of the Periodic Table, e.g. a Group 7 oxide, for instance manganese dioxide.

Typically, the enzyme used as the ROS-quenching agent is catalase or superoxide dismutase, preferably catalase.

In a preferred embodiment, the ROS-quenching agent is a metal of Group 10 or 11 of the Periodic Table or an alloy containing such a metal. In a particularly preferred embodiment, the ROS-quenching agent is a metal of Group 10 or an alloy containing such a metal, more preferably platinum or a gold/silver alloy, most preferably platinum. These metals are particularly useful as the ROS-quenching agent as they have an extremely long lifetime in a device and degradation is not of concern. The metals can also be simply adsorbed to the membrane (either to the surface or preferably within the pores). Immobilisation, for example by covalent attachment of the quenching agent is not required.

When the ROS-quenching agent is a transition metal or a transition metal compound, it is typically present in the membrane in the form of nanoparticles, i.e. particles with a nanoscale average particle size, typically 1-100 nm, for example at least 5 nm, 10 nm or at least 20 nm, and for example up to 90 nm, 80 nm or 70 nm. Nanoparticulate materials are advantageous since they can be provided within the pores of the membrane rather than solely on the surface. Their small size also facilitates an even distribution of the particles through the membrane pores, leading to improved efficiency in quenching ROS.

In the case of nanoparticles, the particles may have any appropriate form or crystal structure. For example, platinum nanoparticles may be in the form of tetrahedron, cube, octahedron, truncated cube, cuboctahedron, truncated octahedron, triangular plate, bipyramid, tripod, decahedron, rod or wire or icosahedron. Platinum nanoparticles may also be produced as spherical particles, hollow structures and dendrites. The various structures and techniques for their preparation are set out in Zhenmeng Peng, Hong Yang, *Nano Today*, 2009, 4, 143-164 and the references cited therein. Brief details of the preparation of these different forms are set out in Table 1 below:

TABLE 1

Pt Nanoparticles Crystal Structures.

| Precursor | Reductant[a] | Surfactant[b] | Additive[c] | Condition[d] | Shape[e] |
|---|---|---|---|---|---|
| $K_2PtCl_4$ | $H_2$ | Na[PA] | pH | RT, 12 h | C, T |
| $K_2PtCl_4$ | $H_2$ | Acrylic acid | pH | RT, 12 h | C, T |
| $K_2PtCl_4$ | $H_2$ | PNIPA | | LCST | C |

TABLE 1-continued

Pt Nanoparticles Crystal Structures.

| Precursor | Reductant[a] | Surfactant[b] | Additive[c] | Condition[d] | Shape[e] |
|---|---|---|---|---|---|
| $K_2PtCl_4$ | $H_2$ | PNEA | | LCST | Tri |
| K2PtCl4 | $H_2$ | PVP, PNIPA, Na[PA] | | RT | Tri, Sq, Hex |
| $K_2PtCl_6$ | $H_2$ | Na[PA] | | RT | C, TO |
| $K_2PtCl_6$ | $H_2$ | PVP | | 25-45° C. | T |
| $H_2PtCl_6$, $K_2PtCl_4$ | $H_2$ | PVP | | RT, overnight | T |
| $K_2PtCl_4$ | $H_2$ | $Na_3$[Cit] | NaOH | RT | C, T, Hex |
| $H_2PtCl_6$ | $H_2$ | PVP | | RT, overnight | Tri, SF |
| $K_2PtCl_6$ | $H_2$ | PVP | | RT | Tet |
| $Na_2PtCl_4$ | PVP | PVP | | 80° C. | Tri, SP |
| $K_2PtCl_6$ | $Na_3$[Cit] | Na[PA] | | Reflux, 3.5 h | SP |
| $K_2PtCl_6$ | $NaBH_4$, $H_2$, AA | TTAB | | 50° C. | C, CO, PP |
| $H_2PtCl_6$ | $NaBH_4$ | CTAB | $AgNO_3$ | RT | C |
| $K_2PtCl_6$ | $NaBH_4$ | CTAB | HCl | RT, 12 h | DD |
| $H_2PtCl_6$ | EtOH | PNIPA | | Reflux | SP |
| $H_2PtCl_6$ | $NaBH_4$, $H_2$ | Pluronic L64 | | RT | SP |
| $H_2PtCl_6$ | $NaBH_4$ | MSA | | | SP |
| $K_2[Pt(C_2O_4)_2]$ $K_2PtCl_4$ $K_2PtCl_6$ | $H_2$ | $K_2C_2O_4$, $CaCl_2$ | | RT or 55° C. | C, Hex |
| $K_2PtCl_4$ | Cu foil | | $Cu^{2+}$ | | C |
| $Na_2PtCl_6$ | Vitamin B2 | Vitamin B2 | | RT | SP |
| $H_2PtCl_6$ | Hydrazine | AOT | Isooctane | RT | SP |
| $K_2PtCl_4$ | γ-ray | CTAB | Hexanol | RT | NR |
| $H_2PtCl_6$ | Hydrazine | Berol 050 | Isooctane | RT | SP |
| $K_2PtCl_4$ | UV, AA | SDS, Brij-35, DSPC | SnOEP, chol | | SP |
| $K_2PtCl_4$ | AgNR | | | | C/S |
| $H2PtCl_6$ | CoNP | | | 95° C. | Hol |
| $H2PtCl_6$ | $H_2$ | Et-HMM | | 200° C. for 4 h | Nec |
| $H_2PtCl_6$ | ED | | | RT | SP |
| $K_2PtCl_4$ | ED | AA | $H_2SO_4$ | RT | THH |
| $K_2PtCl_6$ | ED | | $H_2SO_4$ | RT | NH |
| $Na_2PtCl_6$ | ED | | HCl | RT | NW |
| $K_2PtCl_6$ | ED | | $H_3BO_3$ | RT | NT |
| $H_2PtCl_6$ | γ-ray | | MeOH | RT | SP |
| $H_2PtCl_6$ | UV | | MeOH | RT | NW |
| $PtCl_4$ | Microwave | | α-Glucose | | SP |

Table 1.
[a]PVP = poly(N-vinyl-2-pyrrolidone); Na₃[Cit] = sodium citrate; AA = ascorbic acid; EtOH = ethanol; NR = nanorod; NP = nanoparticle; ED = electrodeposition.
[b]Na[PA] = sodium polyacrylate; PNIPA = poly(N-isopropylacrylamide); PNEA = poly(N-ethylacrylamide); TTAB = tetradecyltrimethylammonium bromide; CTAB = hexadecyltrimethylammonium bromide; Pluronic L64 = $EO_{13}PO_{30}EO_{13}$ triblock copolymer; MSA = mercaptosuccinic acid; AOT = sodium bis(2-ethylhexyl) sulfosuccinate; SDS = sodium dodecylsulfate; DSPC = 1,2-distearoyl-snglycero-3-phosphocholine.
[c]MeOH = methanol; SnOEP = Sn(IV) octaethylporphyrin; chol = cholesterol.
[d]LCST = lower critical solution temperature; RT = room temperature.
[e]C = cube; T = tetrahedron; O = octahedron; THH = tetrahexahedron; CO = cuboctahedron; TO = truncated octahedron; SP = spherical particle; Tri = triangle; Sq = square; Tet = tetragon; Hex = hexagon; NR = nanorod; NW = nanowire; NT = nanotube; Nec = necklace-structure; C/S = core/shell structure; SF = snowflake-like particles; DD = dendrite; PP = porous particles; NH = nanohorn; Hol = hollow structure.

Preferred forms for platinum nanoparticles include cubic, cuboctahedron, dendrite and spherical particles.

Typically, when the ROS-quenching agent is a transition metal or a transition metal compound it present at a loading of 0.01 to 5 wt % of the membrane, preferably 0.1 to 5 wt %, more preferably 0.5 to 3 wt %. The loading can be calculated from the density of the ROS-quenching agent, the uncoated/unimpregnated membrane, and the coated/impregnated membrane.

In some embodiments, the ROS quenching agent is present on the surface of the membrane. In alternative embodiments, the ROS quenching agent is present within the pores of the membrane.

ROS-Quenching Activity

In some embodiments the membrane used in the ROS-quenching barrier layer has an ROS-quenching activity sufficient to quench a solution of $H_2O_2$ having a concentration of 10 ppm, i.e. it can quench a solution having a $H_2O_2$ concentration of at least 10 ppm. The membrane typically has an ROS-quenching activity sufficient to quench a solution of $H_2O_2$ having a concentration of 20 ppm, preferably 50 ppm and more preferably 70 ppm, 80 ppm or 100 ppm.

$H_2O_2$ concentrations are typically measured to an accuracy of +/−2 to 5 ppm. Accordingly, as used herein, where an $H_2O_2$ concentration is indicated this is assumed to be stated to an accuracy of +/−5 ppm. A 400 ppm $H_2O_2$ solution is prepared by diluting a 30% hydrogen peroxide solution (133 μl) in UHP water (100 ml). This 400 ppm solution is diluted to obtain the required concentration. Thus, a 10 ppm solution is obtained by diluting 1 ml of the 400 ppm solution in 39 ml of UHP water. Similarly, a 100 ppm solution is obtained by diluting 10 ml of the 400 ppm solution in 30 ml UHP water.

Figure 4:
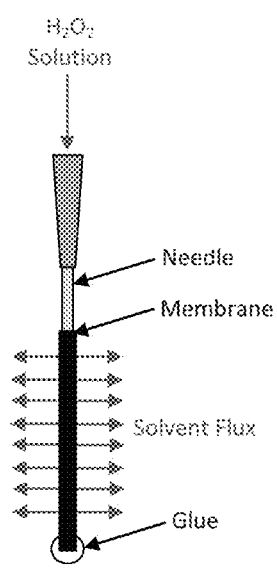
FIG. 4 depicts a schematic version of an apparatus which may be used to determine ROS quenching ability and/or analyte depletion for a membrane.

ROS-quenching activity can be determined by passing up to 100 μl (e.g. 100 μl) of a solution of $H_2O_2$ having a known concentration (e.g. 10 ppm, prepared as set out above)

through a hollow fibre membrane (fibre: inner diameter approx 410 μm; outer diameter approx 500 μm, typical length 25 mm), e.g. using a needle, as schematically represented in FIG. 4, and measuring the $H_2O_2$ concentration of the solution once passed through the membrane. The solution is said to be quenched if the concentration of $H_2O_2$ in the solution once passed through the membrane is less than about 0.5 ppm. When measuring $H_2O_2$ concentration using standard reagent strips known in the art, the detection limit is approximately 0.5 ppm, so that if detection is carried out using such a standard reagent strip, a quenched solution will have a concentration of $H_2O_2$ which is undetectable.

Oxidation of Analyte

The ROS-quenching membrane is typically capable of catalysing the decomposition of ROS without substantially oxidising (or otherwise depleting) analyte (e.g glucose). Thus, preferred ROS quenching agents selectively oxidise ROS, such as $H_2O_2$, over analyte. In some embodiments therefore, the membrane selectively quenches ROS. As used herein, a membrane which selectively quenches ROS typically has an ROS quenching activity sufficient to quench a solution having an $H_2O_2$ concentration of at least 10 ppm, and substantially does not deplete analyte (e.g. it has an analyte depletion rate of 1 mmol/hour or less, preferably 0.05 mmol/hour or less and/or it depletes analyte by no more than 80%, preferably no more than 95% when analyte is passed through the membrane).

The extent of analyte depletion can be determined by passing a solution of analyte (e.g. 100 to 500 μl) having a known concentration through a wall of a membrane (fibre: inner diameter approx 410 μm; outer diameter approx 500 μm, 0.5 mm, typical length 25 mm), e.g. using a needle, as schematically represented in FIG. 4, and measuring the analyte concentration of the solution once passed through the membrane. A membrane which substantially does not deplete analyte will typically produce a concentration of analyte in the solution once passed through the membrane of 80% or more of that of the original solution, typically 85% or more, preferably 90% or more, more preferably 95% or more, most preferably 99% or more.

Alternatively, the rate of depletion can be determined by placing the membrane in a solution of analyte having a known concentration and determining the analyte concentration at regular intervals. Typically, the analyte concentration is determined regularly (e.g. every 8 hours) over a period of at least 24 hours, preferably at least 48 hours. A typical procedure is set out in Example 3, for determining glucose depletion. A membrane which substantially does not cause depletion of analyte typically provides a rate of depletion of no more than 0.1 mmol analyte per hour, preferably no more than 0.08 mmol/hour, more preferably no more than 0.05 mmol/hour.

In some embodiments the extent or rate of analyte depletion is controlled by selecting an appropriate ROS-quenching agent, as described above.

In another embodiment the extent or rate of analyte depletion is controlled by selecting an appropriate ROS-quenching activity, as described above.

In another embodiment the extent or rate of analyte depletion is controlled by selecting an appropriate method for producing the ROS-quenching agent, as described below.

In another embodiment, the extent or rate of analyte depletion is controlled by selecting an appropriate form of nanoparticle, and/or by selecting an appropriate nanoparticle size, as described above.

The Sensor

Figure 1B:
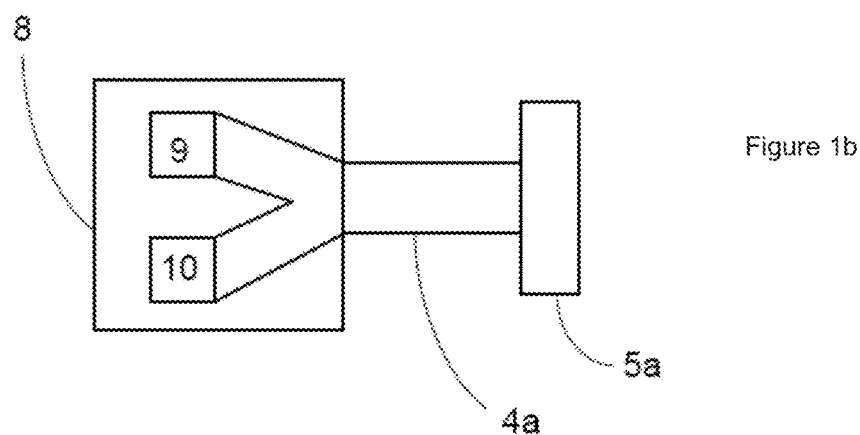

An example of a sensor incorporating an optical fibre is depicted in FIGS. 1a and 1b. The sensor 1 comprises an optical fibre 2 including a sensing region 3 at its distal end. In the case of an invasive sensor, fibre 2 is adapted for insertion into a patient, for example insertion into a blood vessel through a cannula. The sensing region 3 (depicted in more detail in FIG. 2) contains a cell or chamber 7 in which the indicator chemistry is contained. The optical fibre extends through cable 4 to connector 5 which is adapted to mate with an appropriate monitor 8. The monitor typically includes further optical cable 4a that mates with the connector at 5a and at the other end bifurcates to connect to (a) an appropriate source of incident light for the optical sensor 9 and (b) a detector for the return signal 10.

In some embodiments, the sensor is a disposable sensor. The sensor is typically adapted to be connected to a non-disposable monitor including a light source 9 and detector 10.

Figure 2:
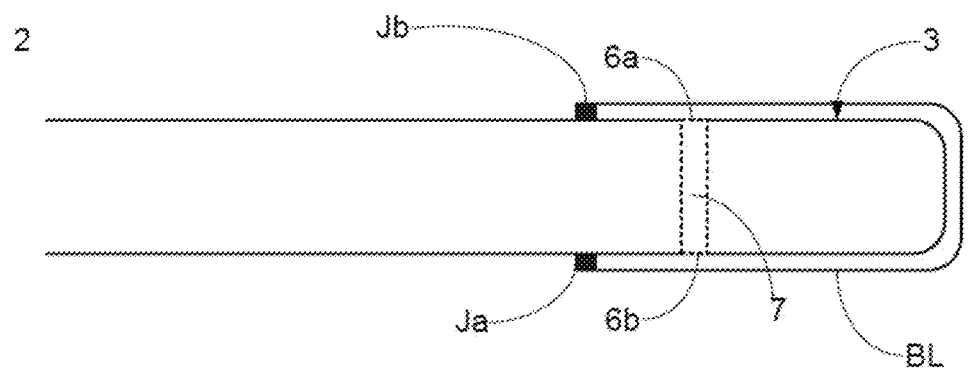
FIGS. 2, 3a and 3b depict various embodiments of a sensing region of a sensor.

As depicted in FIG. 2, the sensing region 3 incorporates a cell 7 in the form of a chamber within the fibre. The cell may take any form, as long as it enables the indicator chemistry to be contained in the path of the incident light directed by the waveguide, here a fibre. Thus, the cell may be attached to the distal end of the fibre or waveguide or may be in the form of a chamber within the fibre having any desired shape.

The cell 7 contains the indicator chemistry. In the case of a glucose sensor, this is typically a boronic acid receptor for binding glucose and a fluorophore associated with the receptor. The emission pattern (e.g. the wavelength, intensity, lifetime) of the fluorophore is altered when the analyte is bound to the receptor allowing optical detection of glucose. The description of the sensor will be given in detail herein with regard to a glucose sensor. However, it is to be appreciated that the ROS-quenching, analyte-permeable barrier layer can be applied to sensors other than glucose sensors.

Sensors having design features in addition to or different from those shown in the attached Figures are of course possible, provided that these include both of the required sensing region and barrier layer. For example, sensors such as those described and illustrated in WO2008/141241, WO2008/098087 and WO2011/113020 can be used.

The receptor and fluorophore may be directly bonded to one another as a receptor-fluorophore construct. Examples of suitable fluorophores are described in WO 2010/116142, the content of which is incorporated herein by reference, and include anthracene, pyrene and derivatives thereof. Examples of suitable boronic acid receptors are compounds having at least one, preferably two boronic acid groups.

In a preferred embodiment, the receptor is a group of formula (I)

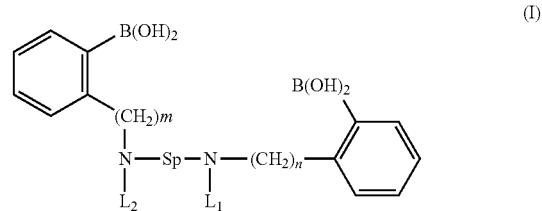

(I)

wherein m and n are the same or different and are typically one or two, preferably one; Sp is an alphatic spacer, typically an alkylene moiety, for example a C1-C12 alkylene moiety, e.g. a C6 alkylene moiety; and L1 and L2 represent possible points of attachment to other moieties, for example to a fluorophore or to a hydrogel. For example, L1 and L2 may represent an alkylene, alkylene-arylene or alkylene-arylene-alkylene moiety, linked to a functional group. Where no attachment to another moiety is envisaged, the functional group is protected or replaced by a hydrogen atom. Typical alkylene groups for L1 and L2 are C1-C4 alkylene groups, e.g. methylene and ethylene. Typical arylene groups are phenylene groups. The functional group is typically any group which can react to form a bond with, for example, the fluorophore or hydrogel, e.g. ester, amide, aldehyde or azide.

Varying the length of the spacer Sp alters the selectivity of the receptor. Typically, a C6-alkylene chain provides a receptor which has good selectivity for glucose.

Further details of such receptors are found in U.S. Pat. No. 6,387,672, the contents of which are incorporated herein by reference.

Further examples of receptors suitable for the sensor include those of formula (II):

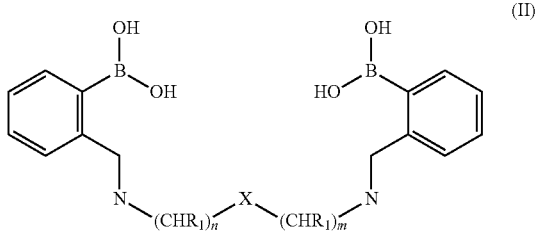

(II)

wherein X represents O, S, $NR_2$ or $CHR_3$;
n is from 1 to 4;
m is from 1 to 4, and n+m is 5;
$R_2$ represents hydrogen or $C_{1-4}$ alkyl;
each $R_1$ is the same or different and represents hydrogen, $C_{1-4}$ alkyl or $C_{3-7}$ cycloalkyl;
or $R_1$, together with an adjacent $R_1$, $R_2$ or $R_3$ group and the carbon or nitrogen atoms to which they are attached, form a $C_{3-7}$ cycloalkyl or a 5- or 6-membered heterocyclyl group, wherein when X represents $CHR_3$, $R_3$ together with an adjacent $R_1$ group and the carbon atoms to which they are attached form a $C_{3-7}$ cycloalkyl group. Further details of receptors of this type are found in U.S. 61/431,756, the contents of which are incorporated herein by reference.

As used herein the term alkyl or alkylene is a linear or branched alkyl group or moiety. An alkylene moiety may, for example, be one in which from 1 to 15 carbon atoms are present such as a $C_{1-12}$ alkylene moiety, $C_{1-6}$ alkylene moiety or a $C_{1-4}$ alkylene moiety, e.g. methylene, ethylene, n-propylene, i-propylene, n-butylene, butylene and t-butylene. $C_{1-4}$ alkyl is typically methyl, ethyl, n-propyl, i-propyl, n-butyl or t-butyl. For the avoidance of doubt, where two alkyl groups or alkylene moieties are present, the alkyl groups or alkylene moieties may be the same or different.

An alkyl group or alkylene moiety may be unsubstituted or substituted, for example it may carry one, two or three substituents selected from halogen, hydroxyl, amine, ($C_{1-4}$ alkyl) amine, di($C_{1-4}$ alkyl) amine and $C_{1-4}$ alkoxy. Preferably an alkyl group or alkylene moiety is unsubstituted.

As used herein an arylene group is an unsaturated group which may be monocyclic, bicyclic, or in which three or four fused rings may be present. Typically, an arylene group is phenylene. Arylene groups may be unsubstituted or substituted. Suitable substituents are $C_{1-4}$ alkyl groups, for example methyl and ethyl. Preferably, an arylene group is unsubstituted.

As used herein a $C_{3-7}$ cycloalkyl group is typically a cyclopentyl or cyclohexyl group. $C_{3-7}$ cycloalkyl groups may be unsubstituted or substituted. Suitable substituents are $C_{1-4}$ alkyl groups, for example methyl and ethyl. Preferably, a $C_{3-7}$ cycloalkyl group is unsubstituted.

As used herein a 5- or 6-membered heterocyclyl group is a 5- or 6-membered saturated ring in which one or more, typically one or two, e.g. one, heteroatom selected from N, O and S is present. Preferred heterocyclyl groups are those in which a nitrogen atom is present, for example piperidinyl and pyrrolidinyl. Heterocyclyl groups may be unsubstituted or substituted. Suitable substituents are $C_{1-4}$ alkyl groups, for example methyl and ethyl. Preferably, a heterocyclyl group is unsubstituted.

The receptor and fluorophore are typically bound to one another and may further be bound to a polymeric matrix such as a hydrogel, or to a dendrimer. Examples of suitable hydrogels and dendrimers are those described in PCT/GB2011/000207, the content of which is incorporated herein by reference.

Alternatively, the first receptor and first fluorophore may be not directly bonded to one another (for example, they may be not bonded to one another or they may be bonded only via a polymeric chain such as a polymeric chain contained within a hydrogel matrix). It will be clear that when the first receptor and first fluorophore are not directly bonded to one another, they must still be capable of interacting in such a way that the fluorescence behaviour of the first fluorophore changes when the indicator system is exposed to glucose. For example, the first fluorophore and the second fluorophore may be capable of binding electrostatically (e.g., as a charge pair), which binding is capable of being at least partly disrupted by the presence of glucose. Examples of suitable first fluorophores include pyranine (HPTS) and its derivatives, such as HPTS itself and the derivatives HPTS-PEG, HPTS-MA, HPTS-$CO_2$, HPTS-Tri-Cys-MA and HPTS-LysMA disclosed in US 2009/0177143, the content of which is herein incorporated by reference in its entirety. Further suitable first fluorophores may include the SNAF and SNAFL dyes commercially available from Molecular Probes. Examples of suitable first receptors include aromatic boronic acids covalently bonded to a conjugated nitrogen-containing heterocyclic aromatic bis-onium structure (e.g. a viologen). Examples of such first receptors are provided in US 2009/0177143, the content of which is herein incorporated by reference in its entirety. One particularly suitable first receptor is 3,3'-oBBV, as described in US 2009/0177143.

Figure 3A:
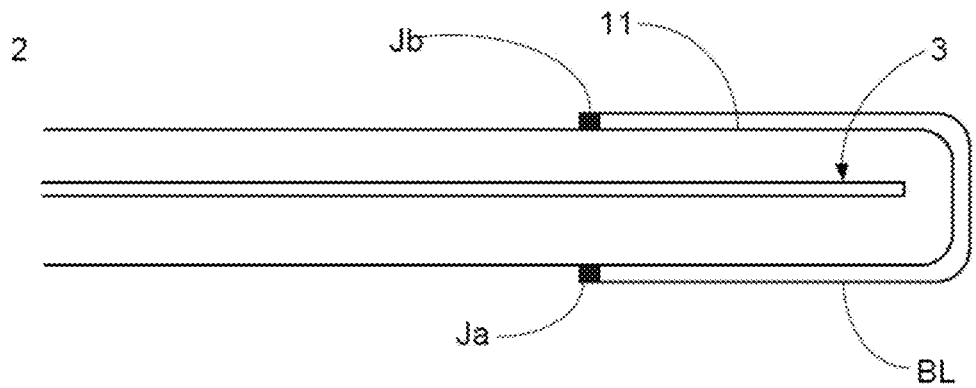
Figure 3B:
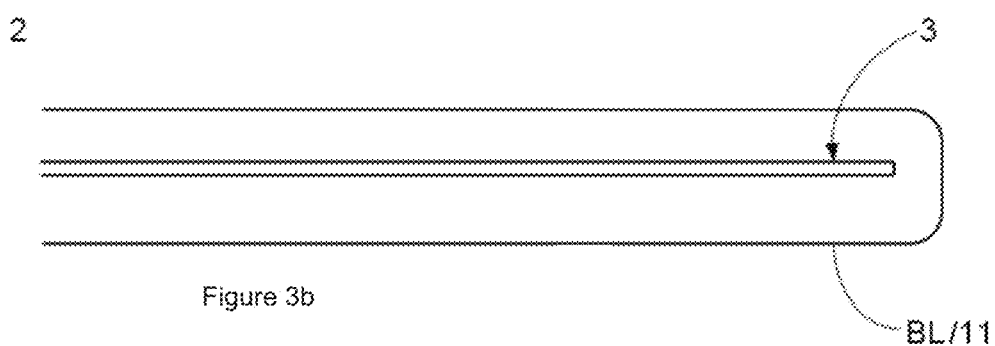

The sensing region 3 of the glucose sensor has one or more openings 6a, 6b to enable glucose to enter the cell. The barrier layer can be provided across these openings so that the sample under test enters the cell through the barrier layer. In FIGS. 2, 3a, and 3b, the barrier layer is provided over the entire sensing region 3. Alternatively, however, the barrier layer may be provided on only part of the sensing region, for example only across openings 6a and 6b.

The sensor is typically designed such that any openings into the sensing region through which the sample under test can pass are covered with the barrier layer. This ensures that passage of $H_2O_2$ into the sensing region is restricted or prevented. In some embodiments, the entire sensing region, or the entire surface of the sensor which is to come into contact with the sample under test, is coated or sheathed with the barrier layer.

As depicted in FIG. 2, the barrier layer BL may be applied directly onto the sensing region, here onto the tip of the optical fibre. This embodiment is appropriate, for example, where the barrier layer is a dialysis membrane. In an alternative embodiment depicted in FIG. 3a, the sensing region 3 is provided on a separate support 11. The separate support structure can provide additional strength compared with the application of the barrier layer directly to the sensing region, and this embodiment is therefore also appropriate for use with dialysis membrane barrier layers. Holes or pores are provided in the support to enable glucose to enter the sensing region 3. Suitable support structures are polymer tubes which are perforated with holes, for example by laser ablation. Microporous hollow fibres which are commonly used in medical oxygenators and which have pores of approximately 0.2 micron in diameter provide appropriate support structures for use with fibre optic sensors. Alternative support structures are woven sheaths of polymeric or metallic materials such as those described in WO2009/019470, the contents of which are incorporated herein by reference in their entirety.

In some embodiments, as depicted in FIG. 3b, the barrier layer itself may form the support structure (BL/11). Preferably, in this embodiment, the membrane used to form the barrier layer is a microporous hollow fibre membrane.

If desired, the barrier layer may be adhered to the surface of the sensor e.g. to the optical fibre itself, or, where relevant, to the separate support structure. This can be achieved by application of a suitable adherent such as cyanoacrylate. Alternatively, where the sensor surface and the barrier layer material are appropriate, the joint between the barrier layer and the sensor can be thermoformed, e.g. at Ja, Jb of FIGS. 2 and 3a.

Method of Manufacture

The sensor is manufactured by providing a sensing region including suitable indicating chemistry (e.g. in the case of a glucose sensor a boronic acid receptor for binding to glucose and a fluorophore associated with said receptor); and providing an ROS-quenching analyte-permeable barrier layer on at least a part of the sensing region; and wherein the sensor is adapted so that analyte enters the sensing region of the sensor through said barrier layer. In the case of an optical sensor the method of manufacture also includes providing an optical waveguide from directing incident light onto the sensor.

In some embodiments, the membrane used in the ROS-quenching analyte permeable barrier layer is formed by vapour deposition. In this embodiment, the ROS-quenching agent is typically a metal or an alloy and the metal or alloy is sputtered under vacuum and at low temperature to form a metal vapour which can be directed toward the membrane for deposition on the membrane surfaces, including those within the pores of the membrane structure.

In an alternative embodiment, the membrane used in the ROS-quenching analyte permeable barrier layer is formed by a method including (i) coating or impregnating a semipermeable membrane, as described above, with an ROS-quenching agent, (ii) washing the membrane and (iii) drying the membrane.

In some embodiments, step (i) comprises wetting a membrane in a suitable water miscible solvent followed by shaking. In a preferred example of this embodiment, the solvent is capable of solvating the pores of the membrane. In some examples of this embodiment the solvent is a polar non-protic solvent. In some examples of this embodiment the solvent is hydrophobic but water soluble. Specific examples of solvents capable of solvating the pores of the membrane include N-methylpyrrolidone (NMP), dimethylsulfoxide (DMSO) and dimethylformamide (DMF). Wetting a membrane with a solvent capable of solvating the pores of the membrane is particularly effective in enabling the ROS quenching agent to be distributed along the length of the pores.

In some embodiments, step (i) comprises immersing a membrane in a solution containing a species capable of forming an ROS-quenching agent (an ROS-quenching precursor) and subsequently subjecting the membrane to conditions such that the $H_2O_2$-quenching agent forms on or in the membrane. In a preferred example of this embodiment, when the $H_2O_2$-quenching agent is platinum, step (i) comprises soaking the membrane in a solution of a platinum containing salt, such as a tetra- or hexa-chloroplatinate salt e.g. sodium or potassium tetrachloroplatinate or sodium or potassium hexachloroplatinate, followed by reduction of the platinum containing salt to platinum metal with a reducing agent such as formic acid, ascorbic acid or hydrazine, preferably formic acid or ascorbic acid, more preferably formic acid. When formic acid is used as the reducing agent, the ROS-quenching precursor is reduced to form an ROS-quenching agent, and the formic acid is oxidised to carbon dioxide gas. This avoids any residue from the reducing agent remaining on the ROS-quenching agent after formation.

In some embodiments the reducing agent may be ascorbic acid or hydrazine, preferably ascorbic acid.

In some embodiments, step (i) comprises shaking and/or heating the membrane whilst under reducing conditions. Thus, for example, the membrane may be contacted with the reducing agent and shaken for a period of up to 7 days, for example at least 2 hours, at least 12 hours or at least 24 hours. Shaking is, for example, carried out at 200 rpm or more, for example up to 400 rpm. This can be achieved at an amplitude of 25 mm on an orbital incubator.

Heating may be carried out concurrently with shaking. Alternatively, either heating or shaking alone is used. Where the membrane is heated whilst under reducing conditions, typically heating is at a temperature of up to 45° C. for a period of up to 7 days, for example at least 2 hours, at least 12 hours or at least 24 hours.

Step (i) may further comprise a washing step (separate from the washing step (ii)). Step (i) may be repeated one or more times, e.g. 1, 2, or 3 times. Where the membrane is immersed in a solution, sonication may be applied to ensure full wetting of the membrane.

Step (i) may further comprise a second reduction, typically after a washing step as described above. Suitable reducing agents for the second reduction include hydrazine and salts of Group 13 hydrides salts such as borohydride salts and aluminium hydride salts, sodium borohydride and lithium aluminiumhydride, preferably sodium borohydride. Preferably the second reducing reagent is hydrazine.

Step (ii) typically comprises soaking the coated or impregnated membrane in water. Typically, the membrane is soaked for at least 12 hours, e.g. at least 24 hours or at least 36 hours. Typically, the water is at a temperature of from 27-47° C., preferably 32-42° C., more preferably 36-38° C. and most preferably about 37° C. Step (ii) typically further comprises immersing the membrane in an organic solvent one or more times, e.g 1, 2, 3, 4 or more times. Preferably the organic solvent is an aliphatic C1 to C6 alcohol, more preferably ethanol.

In some embodiments, step (iii) is carried out under reduced pressure, preferably under vacuum, for one hour or more. In an alternative embodiment, step (iii) is carried out at elevated temperature, preferably at 40-50° C., e.g. about 45° C., for two hours or more.

In some embodiments, the method comprises contacting a barrier layer with a ROS-quenching precursor and a reducing agent; and reducing the ROS-quenching precursor to form a ROS-quenching agent on or in the barrier layer. The process may optionally be repeated one or more times (e.g 1, 2, or 3 times) to provide further layers of the ROS-quenching agent.

In some embodiments the reducing agent is formic acid.

An example of this embodiment is as follows:

A polypropylene hollow fibre membrane is fully wetted by adding a suitable water miscible solvent (e.g. N-methyl-pyrrolidone, NMP) followed by shaking. The solvent is removed from the membrane and fresh solvent (e.g. NMP) is added to the membrane followed by shaking. The removal/replacement/shaking process may be repeated, e.g. three or more times.

The solvent is removed and the following are added to the membrane, with shaking between each addition:
- a suitable water miscible solvent
- UHP water
- 0.05-0.50 mmol (e.g 0.1 mmol) of a platinum containing salt (e.g. a tetra- or hexa-chloroplatinate salt e.g. sodium or potassium tetrachloroplatinate or sodium or potassium hexachloroplatinate)
- formic acid The membrane, in the solution, is shaken at elevated temperature (e.g 30 to 60° C., typically 40-50° C.) for 12 to 24 hours The membrane is washed repeatedly (e.g a minimum of 5 times) in an appropriate solvent system (e.g a mixture of water and a water miscible organic solvent, typically IPA).

The membrane is dried in air at ambient temperature for at least one hour.

In some embodiments, the method comprises contacting a barrier layer with a ROS-quenching precursor and a first reducing agent; partially reducing the ROS-quenching precursor to form a ROS-quenching agent on or in the barrier layer; contacting the barrier layer with a second reducing agent; fully reducing the remaining ROS-quenching precursor to form a ROS-quenching agent on or in the barrier layer. The process may optionally be repeated one or more times (e.g 1, 2, or 3 times) to provide further layers of the ROS-quenching agent.

In some embodiments the first reducing agent is ascorbic acid and the second reducing agent is hydrazine. In another embodiment, the first reducing agent is ascorbic acid and the second reducing agent is a borohydride salt, e.g. sodium borohydride.

An example of this embodiment is as follows:

A polypropylene hollow fibre membrane is fully wetted by adding a suitable water miscible solvent (e.g. propanol). The solvent is removed from the membrane and water is added. This step is repeated until the membrane is fully wetted in water.

0.05-0.10 mmol (e.g 0.06 mmol) of a platinum containing salt (e.g. a tetra- or hexa-chloroplatinate salt e.g. sodium or potassium tetrachloroplatinate or sodium or potassium hexachloroplatinate), ascorbic acid, and a concentrated inorganic acid (e.g. HCl) is added to the solution containing the membrane. The membrane, in the solution, is kept at elevated temperature (e.g 30 to 60° C., typically 40-50° C.) for at least 4 days (e.g 4-7 days, typically about 6 days).

The membrane is washed repeatedly (e.g a minimum of 5 times) in an appropriate solvent system (e.g a mixture of water and a water miscible organic solvent, typically IPA).

$NaBH_4$ is added to the membrane in an appropriate solvent system (e.g a mixture of water and a water miscible organic solvent, typically IPA).

The above steps are repeated, except that the membrane, in the Pt-containing salt/ascorbic acid/inorganic acid solution, is kept at elevated temperature (e.g 30 to 60° C., typically 40-50° C.) for about 1 day.

The membrane is dried in air at ambient temperature for at least one hour.

Another example of this embodiment follows the procedure set out above except that for the first addition of the Pt-containing salt, 0.10-0.20 mmol (e.g 0.12 mmol) is used; and a mixture of a concentrated inorganic acid (e.g. HCl) and hydrazine is used instead of $NaBH_4$.

Use of the Sensor

The present sensor may be used by inserting the sensor into a sample, for instance a sample of body fluid or tissue, e.g. blood, providing incident light to the sensing region of the sensor and detecting the emission pattern of the fluorophore from the emission pattern of the fluorophore. As described above, the emission pattern (e.g. the wavelength, intensity, lifetime) of the fluorophore is altered when glucose is bound to the receptor, allowing an amount of glucose in the sample to be detected and/or quantified.

EXAMPLES

ROS-quenching membranes were produced according to the methods set out below.

Example 1

First Application—Wetting

A polypropylene hollow fibre membrane (fibre internal diameter 416 micron, outer diameter 510 micron, length 25 mm) was fully wetted by adding propanol (3 ml). The solvent was removed from the membrane and UHP water (3 ml) was added. This step was repeated at least 5 times until the membrane was fully wetted in UHP water (3 ml).

First Application—First Reducing Agent

The UHP water was removed from the vial containing the membrane and fresh UHP water (2 ml) added followed by potassium tetrachloroplatinate (50 mg), ascorbic acid (300 mg), and 37% HCl (0.25 ml).

First Application—First Reduction

The membrane, in the Pt/ascorbic acid solution, was placed in an oven and heated at 45° C. for 6 days.

First Application—Second Reducing Agent and Second Reduction

The membrane was washed a minimum of 5 times in an IPA/UHP water solution (70:30 v/v, 7 ml). $NaBH_4$ (50 mg) was added to the membrane in an IPA/UHP water solution (70:30 v/v, 7 ml).

First Application—Washing

The membrane was washed a minimum of 5 times in an IPA/UHP water solution (70:30 v/v, 7 ml). The membrane was fully wetted by adding propanol (3 ml). The solvent was removed from the membrane and UHP water (3 ml) was added. This step was repeated at least 5 times until there was no propanol present.

Second Application—First Reducing Agent

The UHP water was removed from the vial containing the membrane and fresh UHP water (2 ml) added followed by potassium tetrachloroplatinate (25 mg), ascorbic acid (300 mg), and 37% HCl (0.25 ml).

Second Application—First Reduction
The membrane, in the Pt/ascorbic acid solution, was placed in an oven and heated at 45° C. for 1 day.
Second Application—Second Reducing Agent and Second Reduction
The membrane was washed a minimum of 5 times in an IPA/UHP water solution (70:30 v/v, 7 ml). NaBH$_4$ (50 mg) was added to the solution containing the membrane.
Second Application—Washing
The membrane was washed a minimum of 5 times in an IPA/UHP water solution (70:30 v/v, 7 ml). After water washing the membrane was dipped in ethanol (7 ml).
Drying
The membrane was dried under air at room temperature and pressure for a minimum of 1 hour.

Example 2

Figure 5A:
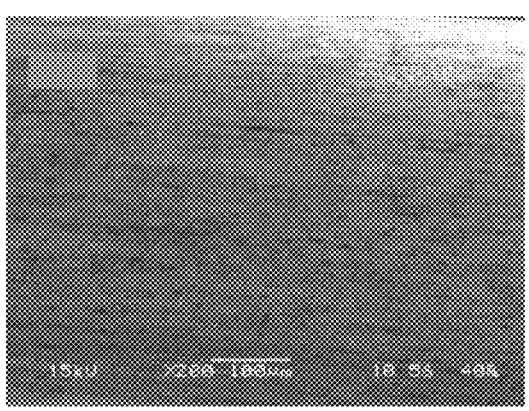
FIGS. 5a-d depict SEM images for the membrane of Example 2.
Figure 5B:
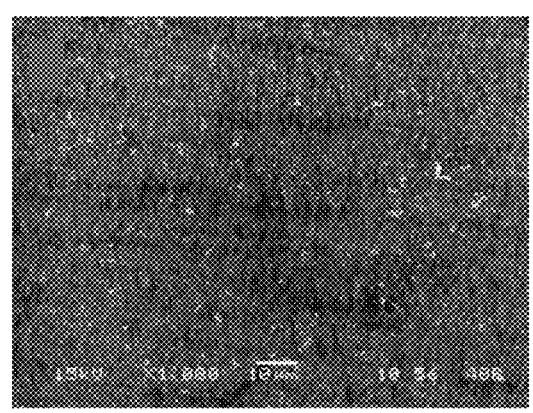
Figure 5C:
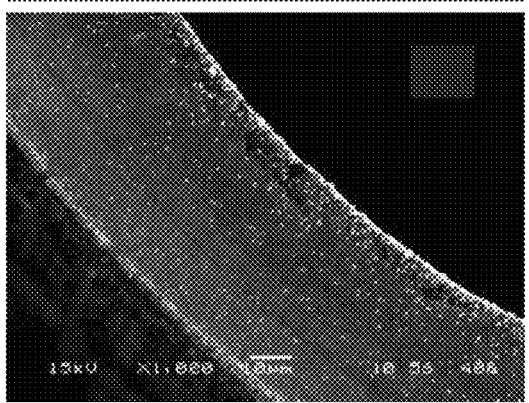
Figure 5D:
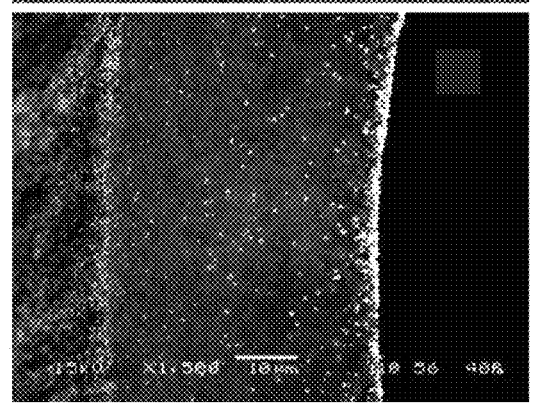

An ROS quenching membrane was produced following the procedure of Example 1 except that:
(v) for the First application—First reducing agent step 50 mg of potassium tetrachloroplatinate was used; and
(vi) for the First application—Second reducing agent steps—Second reducing agent and second reduction steps, a mixture of 37% HCl (0.5 ml) and hydrazine (1.5 ml) was used instead of NaBH$_4$ in an IPA/UHP water solution (70:30 v/v, 7 ml).
SEM images of the membrane are shown in FIG. 5a and FIG. 5b are surface images whilst FIG. 5c and FIG. 5d are cross-sectional images.

Example 3

Hydrogen peroxide solution (10 ppm) was prepared as follows:
A 30% hydrogen peroxide solution (133 μl) was diluted in UHP water (100 ml) to obtain a 400 ppm solution of hydrogen peroxide. To obtain a 10 ppm solution of hydrogen peroxide 1 ml of the 400 ppm solution was diluted in 39 ml of UHP water. 100 μl of the 10 ppm solution thus prepared was pumped through the wall of a 25 mm length of the membrane of Example 1, as schematically depicted in FIG. 4. No peroxide was detected in the solution that had travelled through the membrane. Detection of H$_2$O$_2$ was carried out using peroxide test strips capable of detecting 0.5 ppm or greater peroxide (e.g. EM Quant™). The same procedure was repeated with the membranes of Example 2 and the peroxide levels in the solution which had travelled through the membrane was below detection levels (0.5 ppm).

Glucose depletion of the membrane is tested as follows:
Prepare a D-glucose solution (5 mM) and allow the anomeric ratio to equilibrate (40:60 α/β ratio) before use. Place 10 lengths of the membrane to be tested in a 3.5 ml vial and add the pre-prepared D-glucose solution (3 ml). Add the pre-prepared D-glucose solution (3 ml) to a second, empty, 3.5 ml vial as a control. Measure the D-glucose concentration in both vials using a YSI 2300 Stat plus then incubate the samples at 37° C. Over a minimum period of 24 hours measure the D-glucose concentration a minimum of 3 times. Plot a graph of time vs D-glucose concentration and determine the rate of D-glucose degradation.

Example 4

Figure 7:
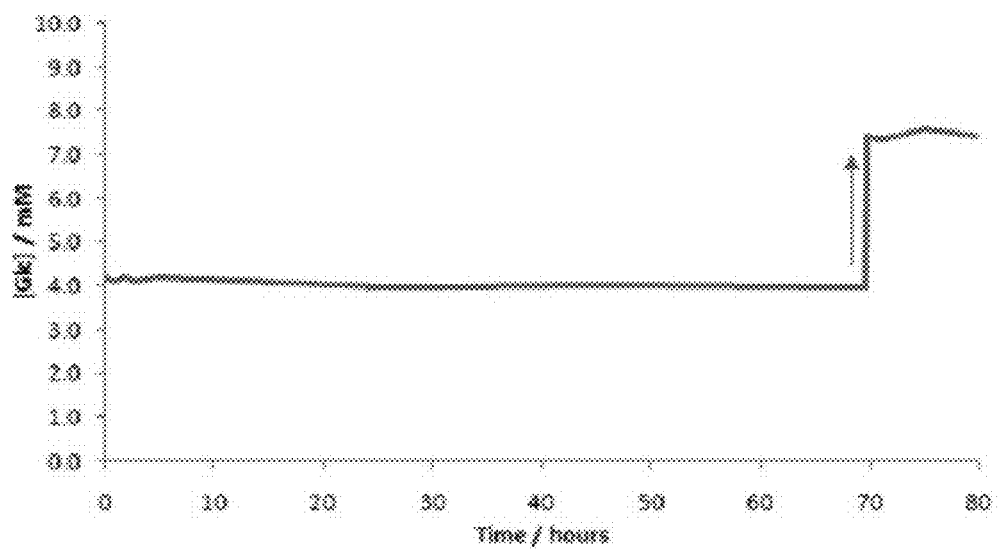
FIG. 7 depicts the results of Example 4.
Figure 8:
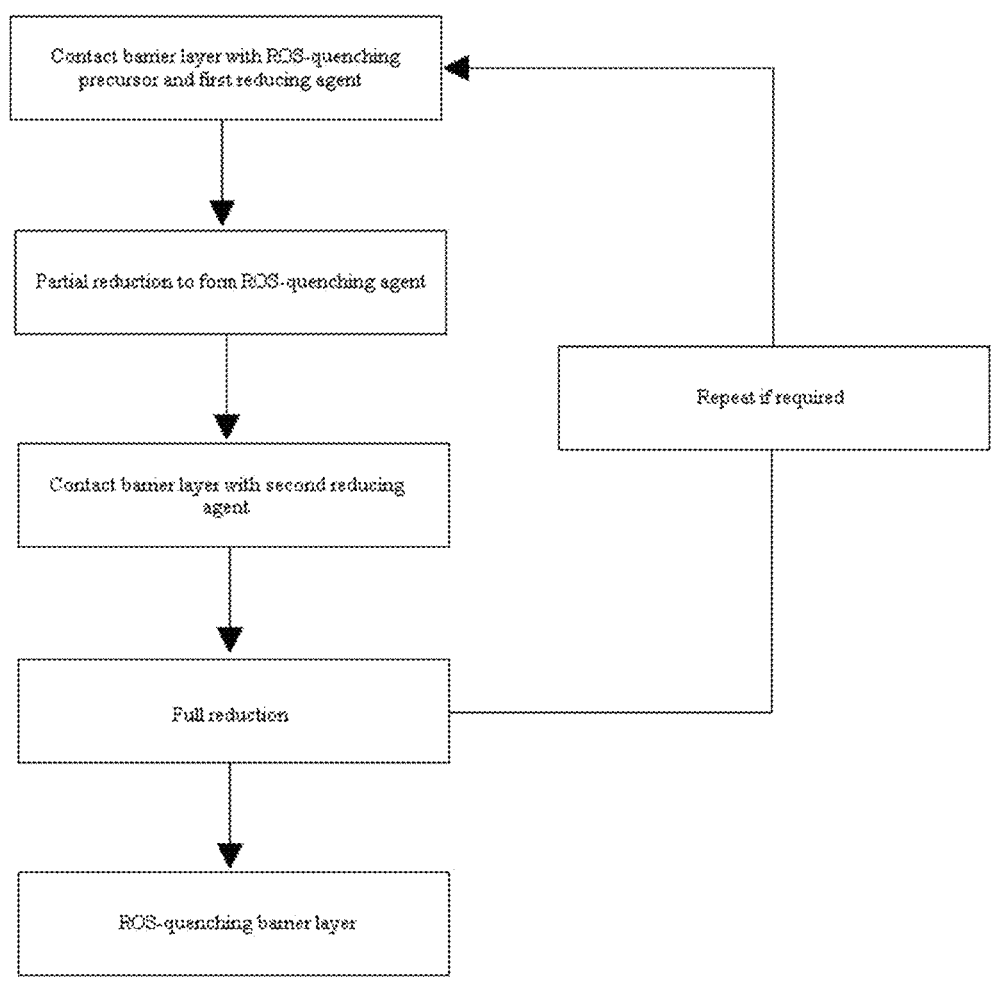
FIG. 8 depicts a schematic view of the process for producing a ROS-quenching barrier layer.

20 lengths (25 mm each length) of the membrane prepared according to the process of Example 2 were placed in a 4.2 mM solution of glucose (3 ml). Glucose concentration was measured against time. After 72 hours, the glucose concentration was increased to 7.4 mM. The results of glucose concentration measurements are shown in FIG. 7. The vertical arrows indicate were the glucose concentration was increased.

The results show no drop in glucose concentration, showing that glucose is stable in the presence of the membranes.

Example 5

ROS-quenching membranes were produced by the processes of Examples 1 and 2 using either a single application of Pt or two applications of Pt. For membranes having a single application of Pt the Second application steps were omitted. The ROS-quenching activities of the membranes were determined by measuring the rate of evolution of oxygen when a 2.5 cm length of the membrane was placed into a 30% hydrogen peroxide solution. The results are given in Table 1 below. Platinum loading is given for certain membranes.

TABLE 1

| Membrane | Pt loading/ wt % | O$_2$ evolved/cm$^3$ · min$^{-1}$ | Process | Notes |
| --- | --- | --- | --- | --- |
| 1 | 0.5 | 12.3 | Ex 1 | Single application |
| 2 | 1.67 | 19.4 | Ex 1 | Two applications |
| 3 | — | 26.0 | Ex 2 | Two applications |

Example 6: In Vitro Testing

Figure 6:
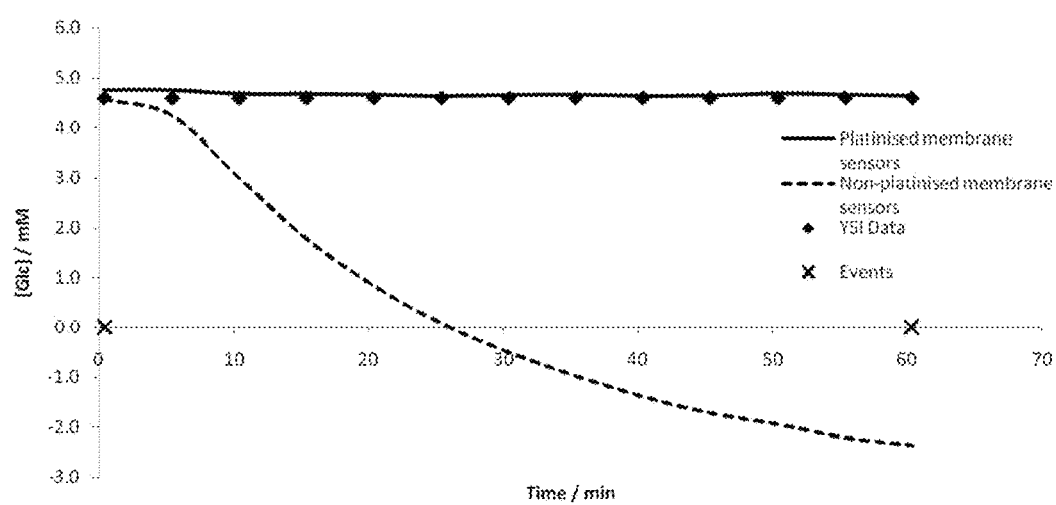
FIG. 6 depicts the results of in vitro testing of a sensor and a corresponding sensor without a platinised membrane.

An optical glucose sensor having an indicator system including a di-boronic acid and a fluorophore associated therewith was constructed with a platinised membrane prepared in accordance with Example 2, such that analyte entering the sensor passed through the membrane. The sensing portion of the sensor was inserted into a 10 ppm hydrogen peroxide solution prepared in accordance with the procedure described in Example 3. The glucose concentration was monitored on a continuous basis using the sensor and also monitored every 5 minutes using an electrochemical glucose sensor (YSI 2300 stat). Testing was continued for 60 minutes and the results are shown in FIG. 6 (solid line).

A corresponding experiment was carried out using an identical sensor, with the exception that the membrane used was not platinised. The results are also depicted in FIG. 6 (dotted line).

Example 7: Effect of Exposure to Peroxide

Platinised and non-platinised sensors as described in Example 6 were calibrated for glucose both before and after exposure to 10 ppm hydrogen peroxide solution. The results are depicted in Table 2 below. No significant changes were observed between the two sensor calibrations of the platinised sensor. In contrast, significant degradation was seen in the non-platinised sensor.

TABLE 2

Calibration constants before and after exposure to peroxide. $I_0$ and $I_\infty$ have been normalised.

| Batch | Sterilised | | $I_0$ | $I_\infty$ | K | Mod$_{5mM}$% |
|---|---|---|---|---|---|---|
| Platinised membrane sensors | Yes | Before | 1.000 | 3.679 | 0.036 | 28.9 |
| | | After | 1.000 | 3.712 | 0.035 | 28.7 |
| | | +/−% | −0.3 | 0.6 | −2.2 | −0.5 |
| Non-platinised membrane sensors | Yes | Before | 1.000 | 2.858 | 0.033 | 20.9 |
| | | After | 1.000 | 1.612 | 0.024 | 6.2 |
| | | +/−% | −22.7 | −56.4 | −26.2 | −70.1 |

Example 8: In Vivo Testing

Figure 9A:
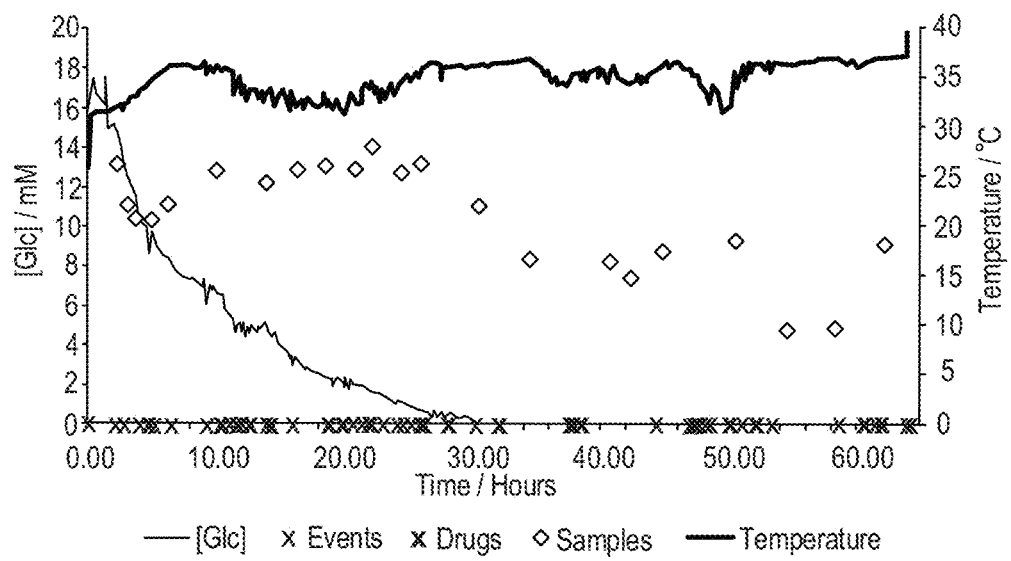
Figure 9B:
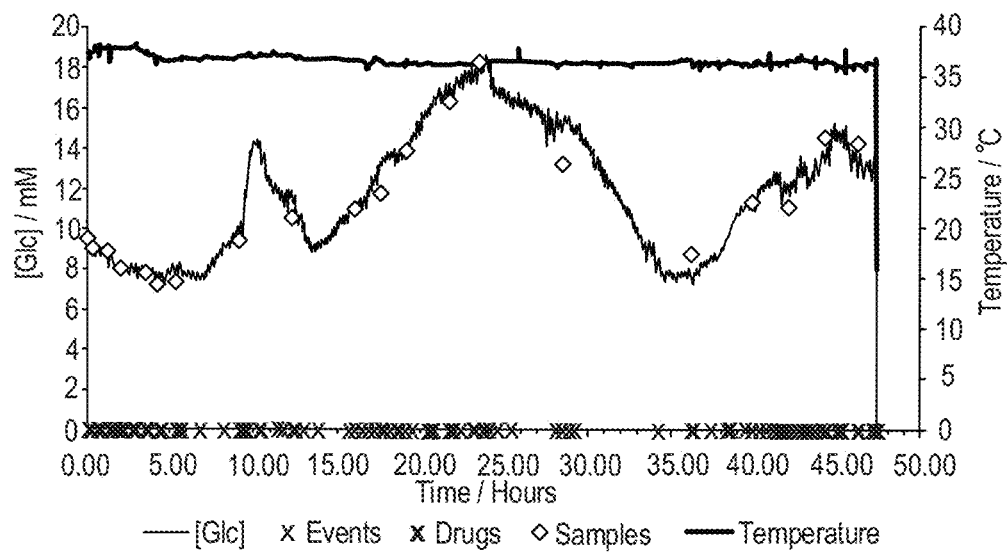

An optical glucose sensor having an indicator system including a di-boronic acid and a fluorophore associated therewith was constructed with a platinised membrane prepared in accordance with Example 2, such that analyte entering the sensor passed through the membrane. The sensing portion of the sensor was inserted into the vein of a patient via a 18G cannular. The glucose concentration as determined by the sensor was recorded on a continuous basis. Whilst testing was carried out, blood samples were taken from the patient approximately every 2 hours, or as needed, and the glucose concentration of each sample determined using an electrochemical glucose sensor (YSI 2300 stat). The results are shown in FIG. 9b.

A corresponding experiment was carried out using an identical sensor, with the exception that the membrane used was not platinised. The results are shown in FIG. 9a. As is apparent from the figures, the results from the sensor having a platinised membrane correspond well with those from the YSI stat, whereas the non-platinised sensor does not show close correspondence with the YSI stat results over the test period.

Example 9

Three sensors were constructed having membranes produced according to the following process:
1. A 25 mm length of polypropylene hollow fibre membrane (MPHF) was placed into a 7 ml vial.
2. The MPHF membrane was fully wetted by adding NMP (2 ml) and the vial shaken. This wetting process was instantaneous and the membrane become translucent on wetting.
3. The solvent in the vial was removed and immediately replaced with NMP (2 ml). The vial was shaken to wash the membrane. This removal/replacement and shaking process was repeated a minimum of three times.
4. The NMP was removed from the vial and the following were added with shaking between each addition:
   NMP (2 ml)
   UHP Water (4 ml)
   Potassium (II) tetrachloroplatinate (0.75 ml of a 50 mg·ml-1 solution)
   Formic acid (0.1 ml)
5. The vial was placed in a heated shaker at 45° C. for a minimum of 12 hours and a maximum of 24 hours.
6. The solvent in the vial was removed and replaced with 70:30 IPA/UHP water (7 ml). This process was repeated a minimum of 5 times until the washings were clear.
7. The membranes were removed from the vial and dried for a minimum of one hour at ambient conditions supported on a straight wire to keep the membranes straight.

Figure 10:
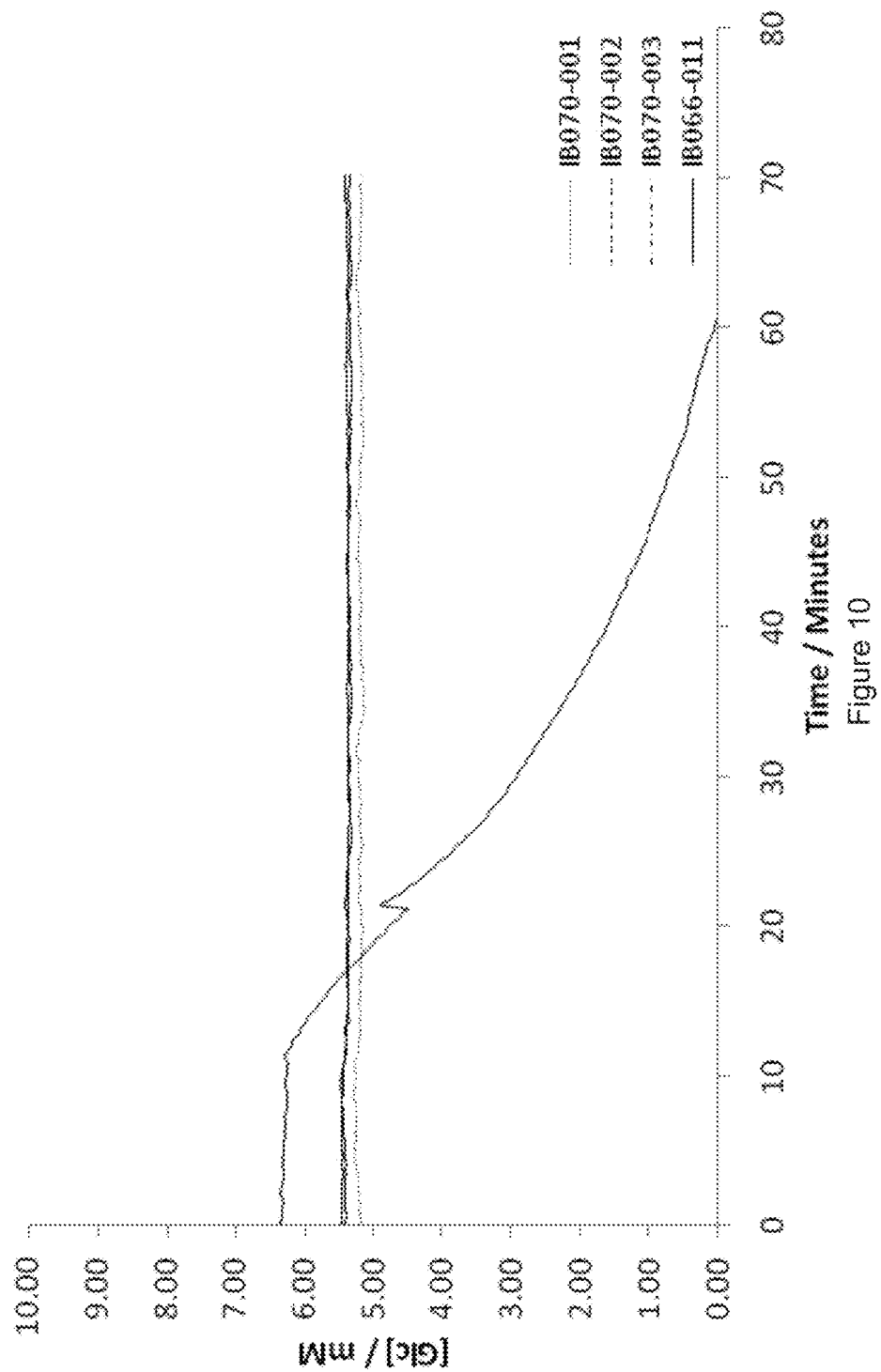
FIG. 10 depicts the results of Example 9. Results for the three platinised sensors are shown as IB070-001, IB070-002, and IB070-003. Results for the unplatinised control are shown as IB066-011.

The sensors were exposed to a 10 ppm solution of hydrogen peroxide for 1 hour, as was an unplatinised control sensor, and the glucose concentration measured. (FIG. 10 shows results for the platinised sensors 1, 2 and 3 as IB070-001, IB070-002, and IB070-003 respectively. Results for the unplatinised control are shown as IB066-011.

These sensors were calibrated before and after this test. Table 3 is a comparison of these calibrations.

TABLE 3

Percentage changes in calibration constants for platinised sensors containing membrane produced according to the procedure of Example 9 (sensors 1-3) when exposed to a 10 ppm hydrogen peroxide solution, as compared to an unplatinised sensor (control)

| Sensor | 1 | 2 | 3 | Control |
|---|---|---|---|---|
| $I_0$ | −0.4 | −0.8 | −1.1 | −21.8 |
| $I_\infty$ | 2.7 | 0.9 | 0.2 | −49.0 |
| K | −5.2 | −3.0 | −0.5 | −16.4 |
| Mod$_{5\ mM}$ | −0.2 | −0.1 | 1.0 | −48.1 |

The platinised sensors appeared to be fully resistant to the hydrogen peroxide solution and there was no significant change in their calibration constants before and after the test. The average modulation at 5 mM glucose changed from 27.47% to 27.53%.

The ROS quenching ability of membranes produced according to the above process was determined in 10 ppm $H_2O_2$ using the procedure of Example 3. The peroxide levels in the solution which had travelled through the membrane was below detection levels (0.5 ppm).

The present invention has been described with reference to a number of particular embodiments and examples. The invention is not, however, limited to these specific embodiments and examples.

The invention claimed is:

1. A sensor comprising:
a sensing region;
a porous barrier layer; and
a reactive oxygen species (ROS)-quenching agent formed on or in the barrier layer;
wherein the sensing region of the sensor defines one or more openings to allow an analyte in a bodily fluid sample to enter the sensing region;
wherein the barrier layer is disposed across the one or more openings to allow the analyte to enter the sensing region through the barrier layer such that the analyte comes into contact with the ROS-quenching agent;
wherein the barrier layer has an ROS-quenching activity sufficient to quench a solution of $H_2O_2$ having a concentration of 10 ppm; and
wherein the sensor is configured such that fluid passing through the barrier layer is in contact with the ROS-quenching agent throughout the time the fluid is moving through the barrier layer.

2. The sensor of claim 1, wherein the ROS-quenching agent comprises platinum.

3. The sensor of claim 2, wherein the ROS-quenching agent comprises platinum in the form of nanoparticles.

4. The sensor of claim 1, wherein an entire sensing region, or an entire surface of the sensor that comes into contact with the sample, is coated or sheathed with the barrier layer.

5. The sensor of claim 1, wherein the barrier layer comprises polypropylene hollow fibres.

6. The sensor of claim 1, wherein the sensing region is provided on a support material.

7. The sensor of claim 1, wherein the barrier layer is provided over the entire sensing region or is provided on only part of the sensing region.

8. A sensor comprising:
a sensing region; and
a porous barrier layer comprising an ROS-quenching agent;
wherein the sensing region of the sensor defines one or more openings to allow an analyte in a bodily fluid sample to enter the sensing region; and
wherein the barrier layer is disposed across the one or more openings to allow the analyte to enter the sensing region through the barrier layer such that the analyte comes into contact with the ROS-quenching agent;
wherein the barrier layer has an ROS-quenching activity sufficient to quench a solution of $H_2O_2$ having a concentration of at least 10 ppm; and
wherein the sensor is configured such that fluid passing through the barrier layer is in contact with the ROS-quenching agent throughout the time the fluid is moving through the barrier layer.

9. The sensor of claim 8, wherein the barrier layer is impregnated with the ROS-quenching agent.

10. The sensor of claim 8, wherein the barrier layer comprises platinum in the form of nanoparticles.

11. The sensor of claim 8, wherein the barrier layer is applied directly onto the sensing region.

12. The sensor of claim 8, wherein the barrier layer substantially does not cause depletion of analyte.

13. The sensor of claim 8, wherein sensing region comprises a receptor and a fluorophore that are bound to one another and to a polymeric matrix.

14. The sensor of claim 8, wherein the sensing region is provided on a support material.

15. The sensor of claim 8, wherein the barrier layer defines pores that have a pore size ranging from about 1 nm to 1 μm and an aspect ratio of at least 100.

16. The sensor of claim 8, wherein the barrier layer defines pores, the pores each having a length, and the ROS-quenching agent is within the pores of the barrier layer and is distributed along the length of the pores.

17. The sensor of claim 8, wherein the barrier layer is a layer formed by vapour deposition of the ROS-quenching agent.

18. The sensor of claim 8, wherein the barrier layer does not allow materials of molecular weight 6,000 or higher to pass through.

19. The sensor of claim 8, wherein the ROS-quenching agent is present at a loading of 0.01 to 5 wt % of the barrier layer.

20. The sensor of claim 8, wherein the barrier layer has an ROS-quenching activity sufficient to quench a solution of $H_2O_2$ having a concentration of 100 ppm.

21. The sensor of claim 8, wherein the barrier layer is provided over the entire sensing region or is provided on only part of the sensing region.

22. A sensor comprising:
a sensing region;
a porous barrier layer; and
an ROS-quenching agent formed on or in the barrier layer;
wherein the sensing region of the sensor defines one or more openings to allow an analyte in a bodily fluid sample to enter the sensing region;
wherein the barrier layer is disposed across the one or more openings to allow the analyte to enter the sensing region through the barrier layer such that the analyte comes into contact with the ROS-quenching agent; and
wherein the sensor is configured such that fluid passing through the barrier layer is in contact with the ROS-quenching agent throughout the time the fluid is moving through the barrier layer.

\* \* \* \* \*